United States Patent
Ferek-Petric et al.

Patent Number: 5,913,879
Date of Patent: Jun. 22, 1999

[54] VENOUS POOLING DETECTION AND THERAPY DEVICE

[75] Inventors: Bozidar Ferek-Petric; Branko Breyer, both of Zagreb, Croatia

[73] Assignee: Pacesetter AB, Järfälla, Sweden

[21] Appl. No.: 08/952,201

[22] PCT Filed: May 8, 1996

[86] PCT No.: PCT/EP96/01933

§ 371 Date: Nov. 6, 1997

§ 102(e) Date: Nov. 6, 1997

[87] PCT Pub. No.: WO96/35476

PCT Pub. Date: Nov. 14, 1996

[30] Foreign Application Priority Data

May 8, 1995 [HR] Croatia .................................. P950278A

[51] Int. Cl.$^6$ ............................. A61N 1/368; A61N 1/36
[52] U.S. Cl. ................................................................ 607/14
[58] Field of Search .................................................. 607/14

[56] References Cited

FOREIGN PATENT DOCUMENTS 0 620 420  10/1994  European Pat. Off. .

OTHER PUBLICATIONS

"Characterization of Subcutaneous Microvascular Blood Flow During Tilt Table–Induced neurally Mediated Syncope," Benditt et al., JACC, vol. 25, No. 1, Jan. 1995, pp. 70–75.

Primary Examiner—William E. Kamm
Assistant Examiner—Carl H. Layno
Attorney, Agent, or Firm—Hill & Simpson

[57] ABSTRACT

An implantable detection and therapy device allow prediction of the vasovagal syncope for use in administering therapy to a subject, the therapy including pacing pulses or drug delivery, or a combination thereof. The detection and therapy device includes a sensor which obtains blood flow velocity data or blood pressure data either in the area of the tricuspid valve or in the superior vena cava. The data are utilized in a control unit to identify the occurrence of venous pooling, which is recognized by the occurrence of a sudden reduction of the peak values of blood flow velocity waves or blood pressure waves. If this sudden reduction of the blood flow velocity waves or blood pressure waves is preceded by a sudden increase in the sinus heartbeat rate, the reduction is identified as being caused by venous pooling. The sudden increase in sinus heartbeat rate is caused by the increased sympathetic activity preceding the vasovagal syncope. The administration of appropriate therapy is then triggered upon the identification of venous pooling.

26 Claims, 6 Drawing Sheets

VENOUS POOLING DETECTION AND THERAPY DEVICE

BACKGROUND OF THE INVENTION

1. Field of the Invention

This invention relates to a detection device for detecting venous pooling in a human body and to the use of this detection device in a therapy device for preventing vasovagal syncope, particularly to the prediction of neurally mediated bradycardia and hypotension.

2. Description of the Prior Art

The exact etiology of vasovagal syncope remains unknown, but parasympathetic and sympathetic activity have been found to participate in the pathogenesis of vasovagal syndrome. Particularly, vasodepressor reaction is caused by the Bezold-Jarisch reflex. There are three modes of vasovagal responses: cardioinhibitory, vasodepressor and mixed response. Accordingly, patients may have profound bradycardia and a major component of vasodilation as well. It has been postulated that vigorous contraction of relatively empty ventricle activates myocardial sensory receptors, which, in susceptible persons, initiates an inhibitory reflex that results in hypotension, bradycardia or both. Vasodepressor reactions are believed to be caused by activation of unmyelinated left ventricular vagal nerve endings known as C-fibers normally being excited by catecholamines, sympathetic nerve stimulation and left ventricular pressure. The most important physiologic finding is that spontaneous vasodepressor reactions often occur in the context of a sympathetic stimulation as a response to the venous pooling. Accordingly, every vasovagal syncope is preceded by the venous pooling, the sudden heart rate increase, and by the vigorous ventricular contractions.

Bradyarrhythmias associated with vasovagal syncope must be treated by permanent pacing. Vasovagal syncope occurs usually in the erect body position with gravitational stress on venous return. The first pacing mode of choice was VVI pacing with hysteresis. U.S. Pat. No. 4,856,523, describes the inclusion of the hysteresis feature in a rate-responsive pacemaker, in an attempt to prevent competition between the pacemaker and the heart's SA node, when the anterograde conduction path is restored. This patent proposes to vary the hysteresis rate as a function of the pacemaker sensor rate, to a predetermined level upon sensing of the natural heart contraction during the escape interval. U.S. Pat. No. 4,363,325 discloses a multiple-mode pacer which automatically switches from an atrial synchronous mode to a ventricular inhibited mode when the intrinsic atrial rate drops below a preset hysteresis rate. Nevertheless, dual chamber pacing assures maximal contribution of atrial contraction to the ventricular filling, maintaining the natural sequence of cardiac activation. The majority of patients suffering from malignant vasovagal syndrome have intact retrograde atrioventricular conduction, which may cause the pacemaker mediated tachycardia. DVI mode of pacing may provoke atrial arrhythmias due to the fact that the atrial pacing pulse occurs irrespective of the atrial spontaneous activity. The best mode of pacing, preventing these problems in pacing therapy, is DDI mode, especially in patients having intact retrograde conduction. That is the mode when a pacemaker acts like the two independent pacemakers inhibited by spontaneous activity (DDI=AAI+VVI). When there is no vasovagal attack, there is no need for cardiac pacing. It is known in the art that the patient's baseline resting rate can fall as low as 50 beats per minute, especially during the sleep. Moreover, DDI pacing rate being 20 beats per minute higher than resting heart rate may provide significant hemodynamic improvement and maintain consciousness during a vasovagal attack. Accordingly, DDI pacing with hysteresis is the most appropriate pacing mode. However, allowing the patient to have a normal low sinus rate during the night and at rest, as well as starting to pace with 20 beats per minute higher frequency than basic rate (for instance during the day) would require special function of a pacemaker.

Such a pacemaker is disclosed in the U.S. Pat. No. 5,284,491. It has a programmable lower rate and upper rate, a programmable lower hysteresis rate corresponding to a lower rate hysteresis interval, and a programmable intermediate rate, an upper pacing rate and a lower pacing rate. A microprocessor measures the average rate of change in the intervals between consecutive ventricular depolarizations, and compares the last intrinsic escape interval to the lower rate hysteresis interval. If the last intrinsic ventricular interval will be longer than the lower rate hysteresis interval, and if the value of average rate of change in the intervals between consecutive ventricular depolarizations is greater than a first preselected value but less than a second preselected value, the pacemaker stimulates at the lower rate hysteresis and thereafter gradually increases the pacing rate up to the intermediate rate while the pulse generator is in the demand mode. A time counter maintains a continuous pacing at the intermediate rate for a predefined period of time, and the pacing rate is gradually decreased down to the lower pacing rate.

In a patient suffering from vasovagal attack and having such a pacemaker implanted, there is a late start of pacing therapy, when vagal reflex has been already initiated and bradycardia occurred. Such a system cannot assure to the patient a significant release of the symptoms. Moreover, cardioinhibitory response is associated with hypotensive reaction that already occurred when the pacing starts. The best mode of pacing would be with a system which initiates the sequential pacing with the rate higher than the resting rate, but prior to the bradyarrhythmic event. Such a mode of pacing would be possible only with the system comprising certain means for prediction of the vasovagal attack.

A kind of system comprising a prediction means for vasovagal syncope has been disclosed in JACC Vol. 25, No. 1, January 1995, page 70 D. G. Benditt et al. Characterization of Subcutaneous Microvascular Blood Flow During Tilt Table—Induced Neurally Mediated Syncope. It was demonstrated by means of the laser Doppler flowmeter, that a tilt-up test causes the subcutaneous blood flow reduction as well as the blood flow oscillations having a specific frequency.

There are several blood flow measurement methods being feasible to be utilized in implantable systems. There is a possibility to measure the impedance by means of the very low current strength, such as disclosed in EP-A-0 620 420. The impedance is modulated by the ionic liquid flow.

Blood flow parallel to the catheter can be measured by means of the system disclosed in U.S. Pat. No. 4,691,709. The catheter employs an elongated optical fibre member wherein the light transmission is modulated due to the pressure acting thereon. The flow velocity is determined as a function of the difference between the total pressure and the transversely acting pressure.

Our invention disclosed in U.S. Pat. No. 5,243,976, No. 5,316,001 and No. 5,318,595 is a novel principle of physiologic cardiac pacing based on the tricuspid blood flow measurement. EP-A-0 740 565 discloses the cardiac pacing system utilizing the blood flow through either right pulmonary veins or superior vena cava as a parameter for pacing control. Apart from the ultrasonic Doppler system, we have also developed the low-power blood flow measurement methods to be utilized in these inventions. The hydrodynamic sensor is disclosed in our U.S. Pat. No. 5,271,408. The ultrasonic system measuring the blood flow by means of an ultrasonic beam being perpendicular to the flow velocity vector is disclosed in EP-A-0 739 183. The galvanic flow sensor is disclosed in EP-A-0 752 826 being a polarizable electrode within the blood flow, having the concentration overvoltage modulated by the flow velocity. All these methods are feasible to be incorporated within the implantable therapy device such as a pacemaker.

SUMMARY OF THE INVENTION

It is an object of this invention to detect a development of the venous pooling by means of a sensor implanted within the right heart.

It is a further object of this invention to deliver an appropriate therapy for prevention of vasovagal syncope before the onset of the vagal reflex and consequent bradycardia and hypotension.

In the invention an implantable detection device is used wherein either the intracardiac or the venous blood flow is a measured parameter for vasovagal syncope prediction. A sudden decrease of said parameter of the said blood flow is caused by a sudden reduction of the preload, said reduction being caused by the impediment of venous return and said venous pooling which decreases the blood volume returning through the caval veins, due to the filling of the venous system in the lower limbs.

The invention comprises a detection means for detection of venous pooling due to impediment of venous return, and furthermore a therapy means for preventing the vasovagal syncope, wherein said therapy means is activated whenever said detection means positively detects said impediment of venous return and development of said venous pooling.

The detection means is capable to detect a sudden reduction of blood flow velocity or blood pressure and a sudden increase of heart rates and delivers a venous pooling detection signal if a sudden reduction of measured blood flow velocity or blood pressure is proceeded with a sudden increase of measured heart rate.

Said detection means is capable to detect sudden reduction of preload being caused by said venous pooling.

The therapy means may provide sequential atrio-ventricular cardiac pacing at the rate higher than the patient's resting heart rate and may deliver a drug bolus preventing the hypotension.

The therapy device may comprise a first cardiac lead adapted to be implanted into the right atrium; a second cardiac lead adapted to be implanted into the right ventricle, said lead having a transducer means thereon to be implanted either inside a heart or a blood vessel for measuring the blood flow; a pacing means for providing cardiac pacing of both right heart chambers; and a processing or control means responsive to the measured blood flow for detecting the sudden development of said venous pooling causing the vasovagal syncope and which initiates the sequential cardiac pacing before the vagal reflex and impending vasovagal syncope occur.

Said first cardiac lead may comprise a hollow channel means for delivery of a drug into the heart chamber. A drug delivery means may deliver a programmable quantity of a drug through the hollow channel means into the heart. Said control means initiates the drug delivery into the heart upon detection of said development of venous pooling or upon detection of said reduction of preload.

Said pacing means may comprise a first electrode for delivery of a pacing signal to the heart and for receiving a sensing signal from the heart, said hollow channel and said electrode being provided on a single cardiac pacing lead which is designed to be implanted into the heart in such a way as that the hollow channel terminates with an aperture within the right atrium and the pacing electrode is located within the right atrium.

Said pacing means may comprise a second electrode for delivery of a pacing signal to the heart and for receiving a sensing signal from the heart, said transducer means and said electrode being provided on a single cardiac pacing lead which is designed to be implanted into the heart in such a way as that the transducer is located in the vicinity of the tricuspid valve or within the vena cava superior and the pacing electrode is located within the right ventricle.

Said drug delivery means may comprise a drug reservoir connected to a drug pump which pumps the quantity of drug through said channel of the said lead into the right atrium, the moment of drug delivery as well as said quantity of drug being controlled by the said control means.

Preferably said control means continuously measures said heart rate and parameters of said blood flow and is capable to detect various waves of said blood flow.

Said control means may for instance measure peak velocities of said waves (A, E, AR, S, D), being said parameters of said blood flow and measure or calculate derivatives of said waves being either accelerations or decelerations of said blood flow and being said parameters of said blood flow.

Said control means activates said therapy means whenever a sudden decrease of any of said parameters of said blood flow is detected.

Said control means may reprogram the rate of a sequential atrio-ventricular pacing mode to the rate being higher than said patient's resting heart rate whenever a sudden decrease of any of said parameters of said blood flow is detected.

The device perferably comprises means for discrimination between early diastolic filling wave and late diastolic atrial filling wave, as well as means for measurement of peak velocities (E, A) of both waves and calculation of accelerations and decelerations of both waves if the transducer is located in the vicinity of the tricuspid valve.

The device preferably comprises means for discrimination between reversal flow wave caused by the atrial contraction, systolic wave caused by the ventricular contraction and diastolic wave caused by the ventricular relaxation, as well as means for measurement of peak velocities (AR, S, D) of all three waves and calculation of accelerations and decelerations of all three waves if the transducer is located within the vena cava superior.

As already described, said control means monitors the course of pathophysiologic events which characterize the impending vasovagal syncope, said course being development of said venous pooling and consequent said reduction of preload, then proceeding onset of sympathetic activity and consequent onset of vagal reflex.

The development of said venous pooling is characterized by a sudden decrease of said peak velocity of any of said waves within the waveform of blood flow or by a sudden decrease of said acceleration or deceleration of any of said waves within the waveform of blood flow.

Preferably said control means comprise means for recognition of said onset of sympathetic activity being characterized that a sudden increase of said heart rate is associated with an increase of said parameters of blood flow, for instance with an increase of said peak velocity of any of said waves of blood flow or with an increase of said acceleration or deceleration of any of said waves of said blood flow.

Preferably said control means monitors the function of variation in time of said peak velocities of any of said waves of blood flow during the course of impending vasovagal syncope.

Preferably said control means can activate a learning algorithm in order to record the specific function of variation in time of any of said parameters of blood flow during the impending vasovagal syncope for a specific person. In this case said control means can recall said specific function of variation in time of any of said parameters of said blood flow, and compare it with the instantaneously monitored function of the variation in time of relevant continuously measured any of said parameters of blood flow for the purpose of detection of state of the impending vasovagal syncope.

Said control means may comprise means for recognition of vagal reflex being the reaction on the previously detected said sudden increase of sympathetic activity as well as for recognition of proceeding decrease of the parasympathetic activity, being the recovery phase.

Said control means may comprise means for recognition of a change of any of said parameters of blood flow being associated with a change of said heart rate, caused by the vagal reflex being the reaction on the previously detected said sudden increase of sympathetic activity. It may comprise means for recognition of decrease, being proceeded after previously detected increase, of peak velocity acceleration or deceleration of any of said waves of blood flow, said decrease of peak velocity acceleration or deceleration being associated with decrease of said heart rate.

Said control means may comprise means for detection of the decrease of said derivatives of any of said waves, said decrease being caused by the vagal reflex which is reaction on the previously detected sudden increase of said derivatives of the any of said waves which was caused by the sudden increase of the sympathetic activity.

Said control means may comprise means for detection of change of any of said parameters of blood flow, said change being caused by the proceeding decrease of the parasympathetic activity, being the recovery phase after the vagal reflex.

Said control means may comprise means for detection of the increase of said peak velocity and said derivatives of said waves caused by the proceeding decrease of the parasympathetic activity, being the recovery phase after the vagal reflex and being associated with the increase of said heart rate.

Preferably said control means reprograms the cardiac pacing rate to a predetermined value lower than the patient's resting rate, upon detection of said recovery phase.

When delivering drugs into the heart said drugs may be selected to prevent the vasodepressor reaction and hazardous systemic hypotension of the patient, being provoked by the physiologically preceding and previously detected sudden development of the said venous pooling.

Preferably said pacing means comprises a pulse generator circuit for providing the atrial pacing signal and a filter-amplifier circuit for recording atrial intracardiac potential, both circuits being electrically connected to said first electrode as well as to said control means.

Said pacing means may also comprise a pulse generator circuit for providing the ventricular pacing signal and a filter-amplifier circuit for recording ventricular intracardiac potential, both circuits being electrically connected to said second electrode as well as to said control means.

Preferably said sensor or transducer means for blood flow velocity measurement is electrically connected to an electronic circuit which is electrically connected to said control means in such a way as to supply said control means with digital data representing the analog signal produced by said blood flow velocity.

Said transducer means may be capable to measure especially the intracardiac pressure or the intravascular blood pressure.

Development of said venous pooling is characterized by a sudden decrease of said intracardiac or intravascular blood pressure being proceeded by the sudden increase of said heart rate.

DESCRIPTION OF THE PREFERRED EMBODIMENT

Figure 1:
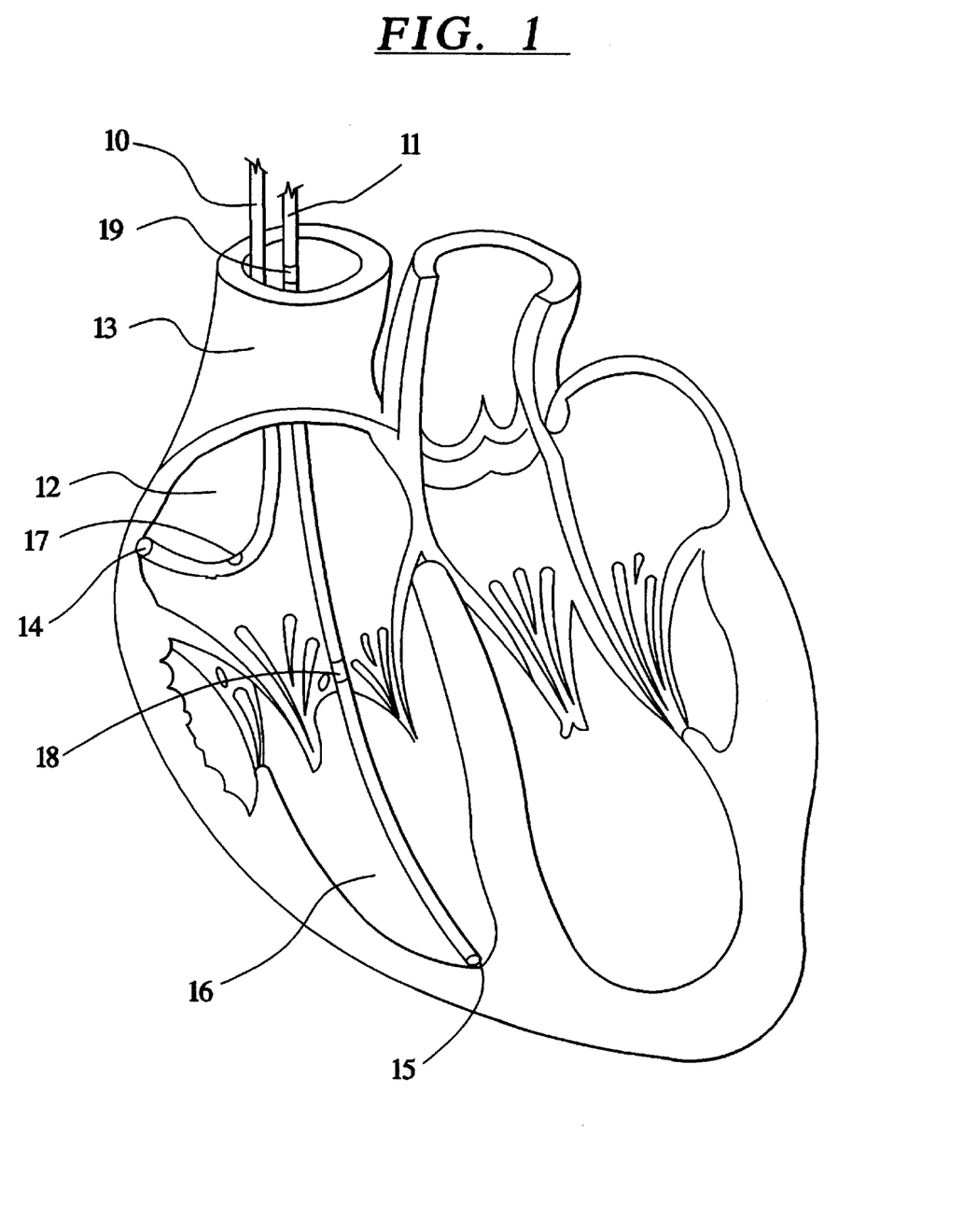
FIG. 1 is a sectional view of a human heart showing the four chambers thereof, with an atrial lead catheter and a ventricular pacing lead implanted therein.

In the embodiment of FIG. 1 there is disclosed a four-chamber cross-section of the human heart having implanted an atrial pacing lead-catheter 10 as well as a ventricular 11 pacing lead. Both leads enter the right atrium 12 through the superior vena cava 13. The atrial lead-catheter has a J-shaped body comprising an electrode 14 on its tip which is positioned in the right atrial appendage. The ventricular lead has an electrode 15 on its tip which is positioned in the right ventricle 16 in the apical position.

The atrial lead 10 comprises a hole 17 within the right atrium 12, which is the termination of a drug delivery catheter tube connecting a drug delivery output pump and the right atrial cavity. Though unipolar leads are disclosed, bipolar leads would be also implanted in the same anatomic relation to the heart chambers. There are two possible and feasible places for blood flow measurement: either the vena cava superior or the tricuspid valve. Accordingly, two flow transducers are shown: a tricuspid flow transducer 18 and a caval flow transducer 19. Only one of the disclosed two transducers will be utilized in a practical system. These transducers could also be pressure transducers for measurement of intracardiac pressure.

Figure 2:
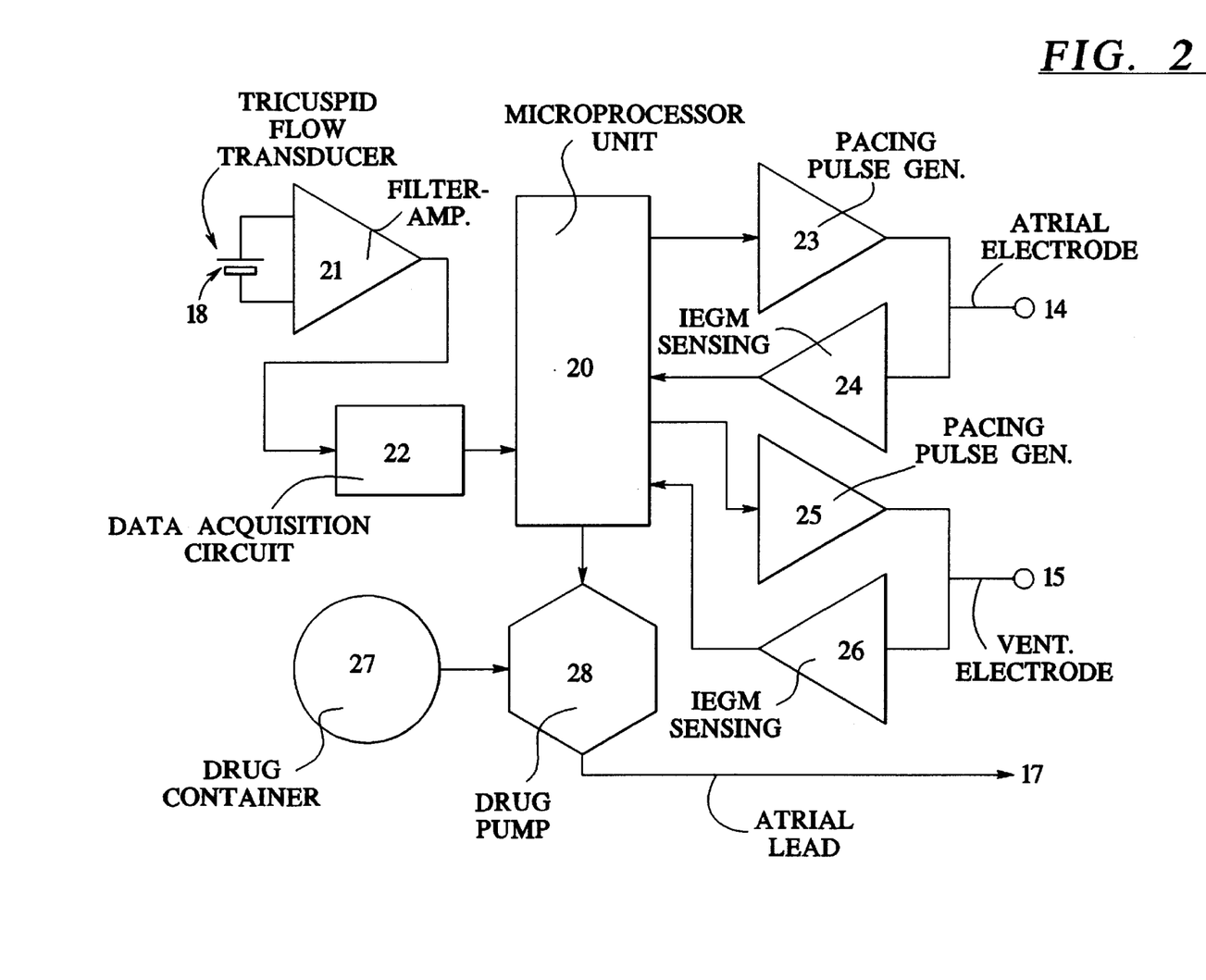
FIG. 2 is a schematic block diagram of a therapy device constructed in accordance with the principles of the present invention.

In the embodiment of FIG. 2, there is disclosed a simplified block diagram of the implantable therapy device (ITD). The entire function of the ITD is regulated and controlled by means of a microprocessor circuit 20. Tricuspid flow transducer 18 being physically mounted on the ventricular lead 11 measures the blood flow in the area of the tricuspid valve. A filter-amplifier 21 and a data acquisition circuit 22 process the signal of the tricuspid flow transducer 18 and supply the microprocessor circuit 20 with a digital form of the signal representing the blood flow. Such a design is feasible for galvanic flow sensor embodiment. The atrial channel of the dual chamber pacing system comprises an atrial pacing pulse generator 23 and an atrial intracardiac EGM sensing circuit 24, being connected with an atrial electrode 14, as it is known in the art. The ventricular channel of the dual chamber pacing system comprises a ventricular pacing pulse generator 25 and a ventricular intracardiac EGM sensing circuit 26, being connected with a ventricular electrode 15, as it is known in the art. Though connection of one pole of each circuit 23, 24, 25, and 26 is shown, it is obvious and known in the art that in disclosed unipolar system, the ITD metal case (not shown) is used as another pole being common one for all four circuits. Moreover, the battery used as a power supply is not disclosed because it is an obvious detail described in numerous prior art references. The ITD additionally comprises a drug container 27 and a controlled drug pump 28 which delivers the required quantity of drug through the atrial pacing lead-catheter 10 by means of the release of a bolus or more of them through the hole 17 within the right atrium.

Figure 3:
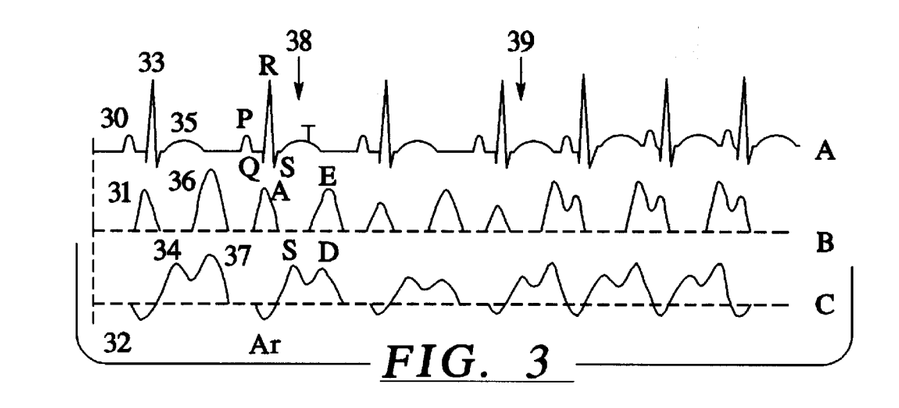
FIG. 3A–3C show various waveforms used for measurements in accordance with the invention.

In FIG. 3, there are disclosed three waveforms in exact timing correlation which can be used in this invention. Though an intracardiac electrogram would be utilized in a practical system, there is a sample of a surface ECG waveform in FIG. 3A illustrating the sinus rhythm comprising P-waves followed by the QRS complexes and consequently the T-waves. A sample of the tricuspid flow waveform is disclosed in FIG. 3B comprising early diastolic filling waves E and late atrial filling waves A. A sample of the venous flow waveform is disclosed in FIG. 3C comprising atrial retrograde flow waves Ar, systolic waves S and diastolic waves D.

FIG. 3B shows the corresponding signal of the blood flow transducer 18 implanted in the area of the tricuspid valve and FIG. 3C shows the corresponding signal of the blood flow transducer 19 implanted within the vena cava superior. The sinus rhythm is initiated by the P-wave 30 being the atrial depolarization, followed by the atrial filling A-wave in the tricuspid area 31 and the retrograde atrial wave in the vena cava superior 32 caused by the subsequent atrial contraction. After a normal atrio-ventricular conduction, the QRS complex 33 occurs representing the ventricular depolarization. Subsequent ventricular contraction causes the systolic S-wave 34 in the caval flow waveform. The ventricular repolarization represented by the T-wave 35 proceeds after the QRS complex and the ventricular relaxation occurs causing the early rapid diastolic filling wave 36 and the diastolic wave 37. If venous pooling suddenly occurs at the moment depicted by an arrow 38, the peak velocities of all waves of the measured flow suddenly decrease. Decrease of the first derivatives of the blood flow waves occur too, being either accelerations or decelerations of the blood flow. This phase of venous pooling development lasts much longer than it is disclosed to last only during a period of few heart beats. This is because there is no place on the paper to illustrate such a long strip which would disclose physiologic time course of events lasting five minutes and more. At the moment depicted by an arrow 39, sympathetic activity increases causing sudden increase of the heart rate which normally precedes the vagal reflex. Vigorous ventricular contractions of almost empty ventricle occur in this phase.

Figure 4:
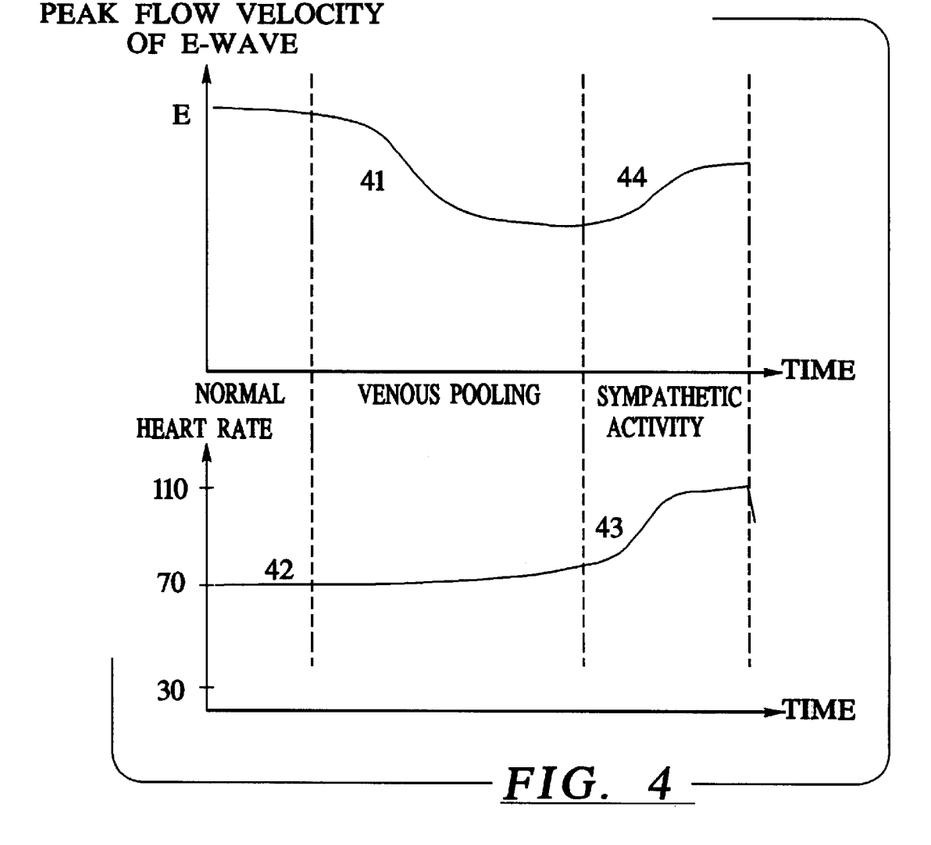
FIG. 4 shows the variation in the heart rate and peak early diastolic velocity before the vasovagal syncope.

FIG. 4 demonstrates the variation of heart rate and the E-wave peak velocity of tricuspid blood flow throughout the time cycle of a period preceding cardioinhibitory vasovagal syncope, in order to clarify detection algorithm of this invention. The period disclosed is approximately 10 minutes long but may be longer or shorter in various patients. This figure illustrates the time course of physiologic events which FIG. 3 fails due to the short strip. The upper waveform is the peak early rapid filling diastolic velocity E and the lower waveform is the heart rate, both being disclosed as functions in time. Three phases of events are demonstrated.

Gravitational stress on venous return can cause the venous pooling. During the normal sinus rhythm 42, the venous pooling causes a sudden drop of blood flow velocity 41. Emptying the right ventricle due to the venous pooling significantly impedes the cardiac contractions. As a consequence, the phase of increased sympathetic activity proceeds. In that phase, vigorous ventricular contractions of almost empty ventricle are developed by a sinus rhythm of distinct increase of the heart rate 43. The peak velocity of filling waveform slightly increases 44. After a minute or few, the vagal reflex and remarkable parasympathetic tone abruptly decrease the heart rate which is known as a cardioinhibitory reflex causing the syncope. The flow velocity waveform conforms with the exhibition of the heart rate. Accordingly, monitoring the heart rate as well as the blood flow, enables detection of the presyncopal period. In this invention, blood flow is measured either by means of a sensor in vena cava superior or in tricuspid valve area. A learning algorithm for every particular patient may be utilized for detection of impending vasovagal syncope, based upon the learning of functions disclosed in this figure. The patients suffering from vasovagal syncope always undergo a tilt-up test, as described in medical literature, in order to provoke the syncope. There is a possibility to activate the learning algorithm by means of an external programmer button at the tilt-up test procedure, in order to record the particular pattern of change of the heart rate and blood flow pattern.

Figure 5:
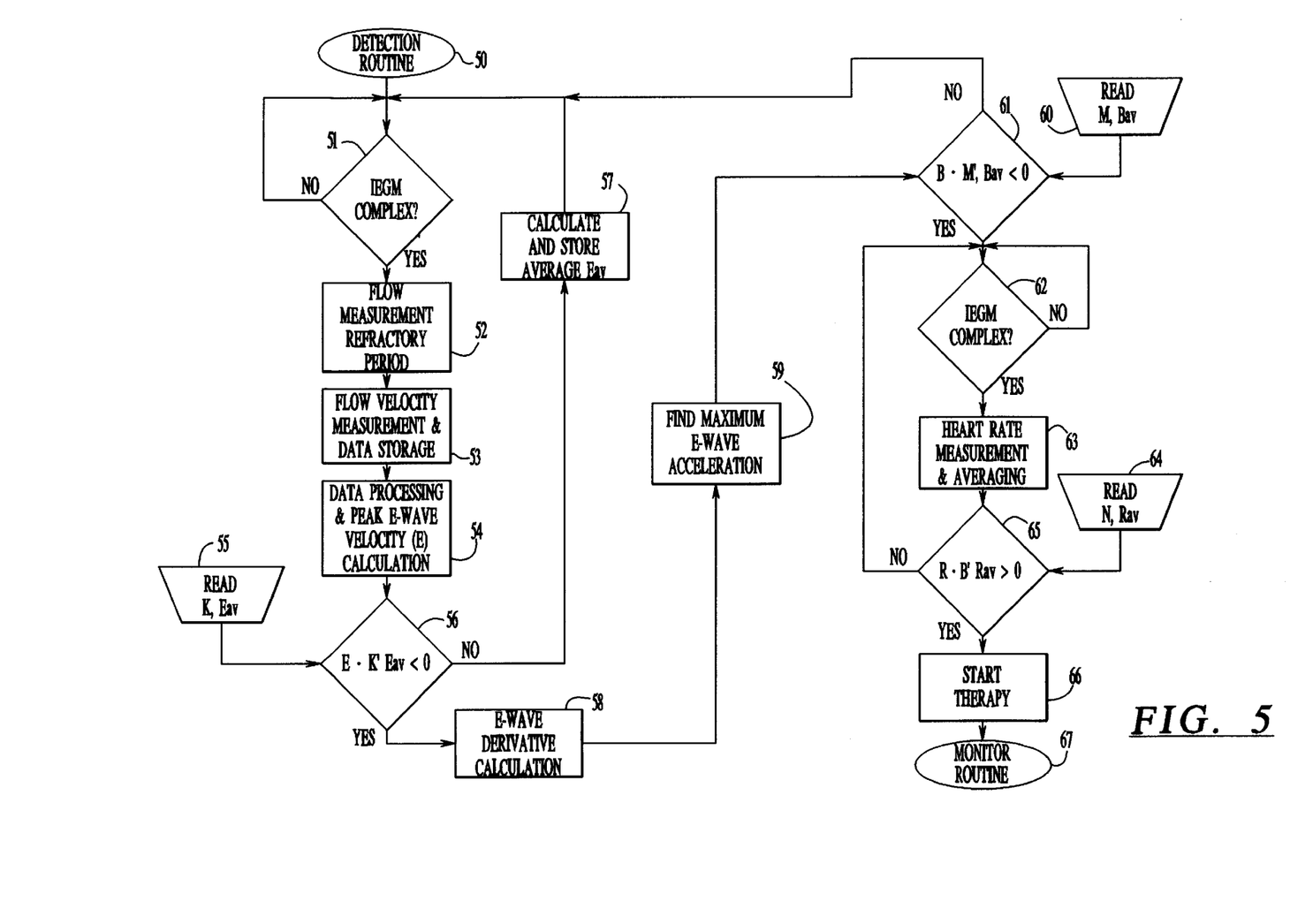
FIG. 5 is a flowchart showing how the microprocessor of the invention polls various functions for providing detection of venous pooling on the basis of blood flow velocity measurement, in accordance with the principles of the present invention.

FIG. 5 is a flow chart disclosing detection routine 50 used for recognition of development of the venous pooling and consequent sympathetic activity prior to impending vasovagal syncope. The waiting loop 51 for sensing of the intracardiac electrogram (IEGM) looks for timing reference signal being the moment of the IEGM occurrence. The IEGM sensing starts (step 52) the flow measurement refractory period. Flow velocity measurement interval starts (step 53) at the end of the flow measurement refractory period. The measurement timing is disclosed in detail in the embodiment of FIGS. 2 of our U.S. Pat. No. 5,243,976 and No. 5,316,001, as well as in our European Patent Application EP-0 474 958A2. Flow charts of the same relevant patent documents disclose in details how the microprocessor polls various functions in order to measure the tricuspid flow velocity. If the flow is measured within the vena cava superior in the manner such as disclosed in our International Patent Application No. PCT/EP95/00246 (publication No. WO 95/19806), the flow will be measured within the cardiac cycle as it is clearly disclosed in FIG. 6 of the relevant PCT application.

Nevertheless, utilizing the tricuspid flow measurement, here is an example if parameters of early diastolic rapid filling wave (E-wave) are utilized for detection algorithm. Processing of the stored flow velocity data (step 54) is done in order to calculate parameters of the E-wave, particularly the instantaneous peak velocity E. Previously stored average peak flow velocity (Eav) and multiplication factor K are recalled (step 55) from the memory for comparison (step 56) with the instantaneous value of measured peak flow velocity E. Venous pooling causes the reduction of preload which also means that there is a reduction of blood flow volume inflow. The factor K may be programmed for every individual patient as a characteristic value for venous pooling development and consequent reduction of preload, and will be in practice the number between 0.4 and 0.7. If the instantaneous peak flow velocity E falls below the value of the product of K and Eav, then calculation (step 58) of the E-wave first derivative is initiated. If there is no significant decrease of peak flow velocity E, the measured instantaneous value of the peak velocity E is used for calculation and storage (step 57) of the new value of the average peak flow velocity Eav.

The point of the maximal blood flow acceleration is a representative value of the instantaneous blood flow acceleration B for further calculations and therefore the maximum E-wave acceleration is calculated (step 59) including the operation of its averaging and consequently storage of the value Bav in a memory. Stored average flow acceleration Bav and multiplication factor M are recalled (step 60) from the memory for comparison (step 61) with instantaneous value of calculated (step 59) flow acceleration B. The factor M may be programmed for every individual patient. If there is no significant decrease of flow acceleration B, detection routine starts from the beginning. If the instantaneous flow acceleration B falls below the value of the product of M and Bav recalled from the memory, it is considered that sudden reduction of blood volume inflow caused previously detected sudden decrease of peak E-wave velocity and now sudden decrease of E-wave acceleration. It is probably caused by the venous pooling which means that there is a hazard of vasovagal syncope. In fact, we use the cross-check algorithm to detect decrease of peak E-wave velocity associated with decrease of the E-wave acceleration for the purpose of sudden reduction of preload. Instead of disclosed method, we could also utilize calculation of E-wave integral representing the blood volume. Detection of sudden decrease of the E-wave integral value would gain the equivalent results in detection of venous pooling. Furthermore, the sudden onset of sympathetic activity is anticipated as a normal feedback event within the autonomic nervous system. Therefore the proceeding intracardiac EGM sensing event is expected (step 62) for measurement and averaging (step 63) of the heart rate. Averaging is done over the previously determined cardiac cycles in order to obtain the reference heart rate during the normal patient's state. Stored average heart rate Rav and multiplication factor N are recalled (step 64) from the memory for comparison (step 65) with instantaneous heart rate. If a significant increase of heart rate is detected, there is obviously an onset of the sympathetic activity. Due to the fact that the vagal reflex may now occur, causing sudden bradycardia and decrease of the systemic blood pressure, a therapy can be initiated (step 66) in order to prevent the vasovagal syncope. The therapy may include sequential pacing at the rate higher than patient's resting rate in order to prevent the bradycardia caused by the vagal reflex which normally proceeds after the temporary heart rate increase caused by the sympathetic activity. The therapy may include the delivery of an antihypotensive drug bolus. A monitoring routine (step 67) may be initiated for detecting cessation of the hazard for vasovagal syncope development.

Figure 6:
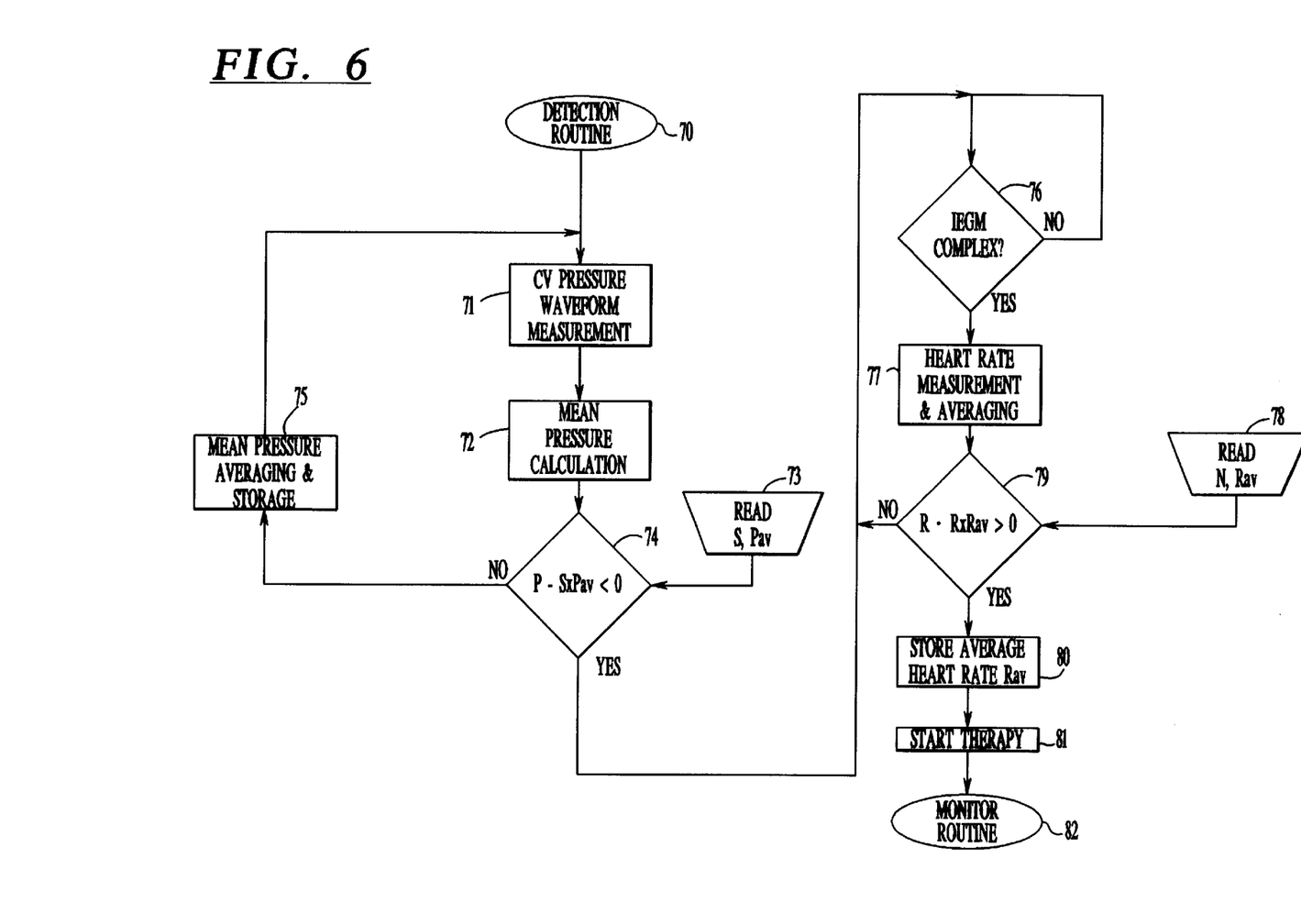
FIG. 6 is a flowchart similar to that of FIG. 5, illustrating detection of venous pooling on the basis of blood pressure measurement, in accordance with the principles of the present invention.

FIG. 6 is a flow chart disclosing detection routine 70 for recognition of development of the venous pooling prior to impending vasovagal syncope, in the same manner as disclosed in FIG. 5, however utilizing an intracardiac pressure sensor. For example, the pressure sensor and the lead design such as disclosed in U.S. Pat. No. 4,600,017 may be used for the purpose, if positioned within the right atrium. The continuous measurement (step 71) of the central venous pressure (CV-pressure) is running. Mean value is used for detection algorithm and therefore the calculation (step 72) of mean pressure value has to be done. Previously stored average mean central venous pressure Pav and multiplication factor S are recalled (step 73) from the memory for comparison (step 74) with instantaneous value of measured and calculated mean pressure Pav. The factor S may be programmed for every individual patient as a characteristic value for venous pooling development and consequent reduction of preload, and will be in practice the number between 0.4 and 0.7. If the instantaneous mean pressure falls below the value of product of S and Pav, it may be caused by the venous pooling. The intracardiac electrogram waiting loop (step 76) is initiated. If there is no significant decrease of mean pressure P, the measured instantaneous value of P is used for calculation and storage (step 75) of the new subsequent value of the average mean pressure Pav.

If the proceeding intracardiac EGM sensing event (step 76) occurs, the heart rate measurement and averaging over the predefined cardiac cycles (step 77) is done. Previously stored average heart rate Rav and multiplication factor N are recalled (step 78) from the memory. If a significant increase of the heart rate proceeds (step 79), the onset of sympathetic activity occurred. Average heart rate is stored (step 80) and a therapy can be initiated (step 81). The monitoring routine 82 may be initiated for detecting cessation of the hazard for vasovagal syncope development. The part of a routine of steps 76, 77, 78 and 79 is the waiting loop for recognizing the sudden onset of the sympathetic activity characterized by sudden increase of the patient's heart rate which occurs as a reaction on the preload reduction.

Figure 7:
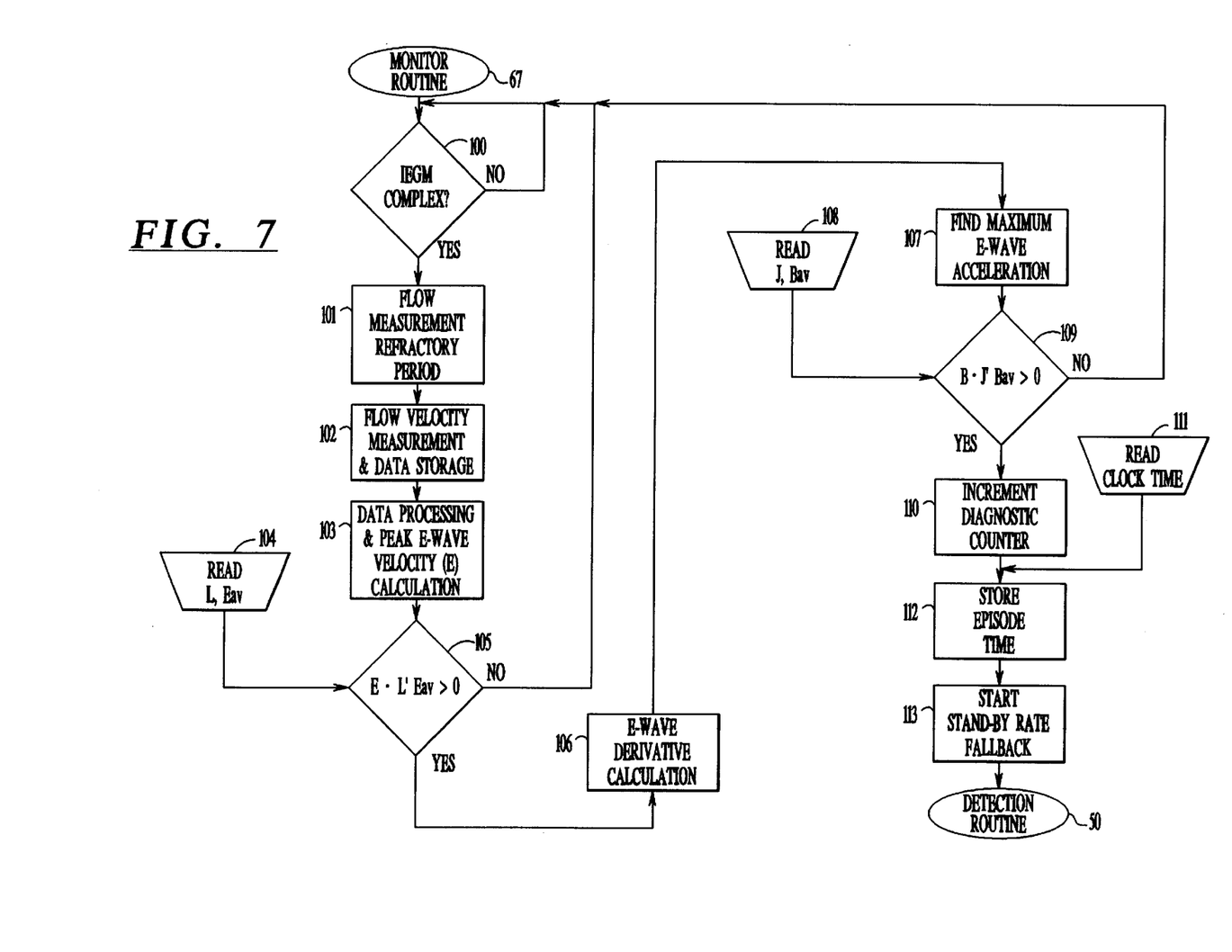
FIG. 7 is a flowchart illustrating a mode of monitoring the physiologic states during impending vasovagal syncope, in accordance with the principles of the present invention.

FIG. 7 is a flow chart illustrating one possible mode of monitoring of the physiologic states during the impending vasovagal syncope following the sympathetic activity increase until detection of recovery phase such as disclosed in FIG. 4. Though routine for tricuspid blood flow measurement is disclosed, the similar routine may be designed for intracardiac pressure measurement. The monitoring routine 67 starts with ventricular intracardiac electrogram detection (step 100). Upon the onset of intracardiac electrogram signal, the previously described blood flow velocity measurement (steps 101, 102 and 103) is initiated. The blood inflow recovery phase detection loop follows, comparing the instantaneous value of peak velocity E with the average value EAV (step 105) recalled (step 104) from the memory together with previously programmed constant L. If the value of peak velocity E increases over the value of product of L and Eav, the recovery of blood flow acceleration has to be detected. Therefore the maximum E-wave acceleration is calculated (step 107) including the operation of its averaging and consequently storage of the value Bav in memory. Stored average flow acceleration Bav and multiplication factor J are recalled (step 108) from the memory for comparation (step 109) with instantaneous value of calculated (step 107) flow acceleration B. If there is no significant increase of flow acceleration B, monitoring routine starts from the beginning. If the instantaneous flow acceleration B increases over the value of product of J and Bav, it is considered that the recovery of blood volume inflow caused previously detected sudden increase of peak E-wave velocity and now increase of E-wave acceleration. The both factors L and J may be programmed for every patient characterizing the recovery phase in every individual patient. Despite of the fact whether the episode of impending vasovagal syncope was symptomatic or asymptomatic due to the ITD therapy, it is beneficial to record the episode for ITD efficiency evaluation. Accordingly, diagnostic counter has to record (step 110) the vasovagal reflex and recovery despite of the fact whether it has caused the syncope or not. The time of the episode is read (step 111) and stored (step 112). The fallback of the pacing rate has to start (step 113) in order to obtain the pacing rate being lower than the resting rate during the night, in order to avoid unnecessary pacing. Detection routine 50 may be initiated again.

It is known in the art that numerous other algorithms may be used for various diagnostic purposes. Moreover, there are other physiologic parameters enabling the sympathetic and parasympathetic activity detection, as it is known in the art: QT interval, QRS potential gradient, ventricular pressure derivative, etc. However, the tricuspid or caval blood flow velocity as well as the central venous pressure measurements are considered to be the only methods enabling direct detection of venous pooling. Moreover, the tricuspid and caval flow velocity measurements enable the monitoring of the autonomic nervous system activity due to the fact that flow waveform parameters are significantly modified by sympathetic and parasympathetic activity variation. As a conclusion, only blood flow velocity parameters enable both features necessary for impending vasovagal syncope detection: the venous pooling detection and the autonomic regulation monitoring.

Although modifications and changes may be suggested by those skilled in the art, it is the intention of the inventors to embody within the patent warranted hereon all changes and modifications as reasonably and properly come within the scope of their contribution to the art.

We claim as our invention:

1. A detection device for detecting venous pooling in a human body, comprising:
    a lead adapted for implantation in a subject and carrying sensor means for obtaining blood flow velocity data, said blood flow velocity data including data identifying at least one blood flow velocity wave produced after each heartbeat;
    means for obtaining heartbeat data identifying successive heartbeats of said subject; and
    control means, supplied with said blood flow velocity data and said heartbeat data, for identifying respective measured values of successive occurrences of said at least one blood flow velocity wave and for generating a signal indicating detection of venous pooling if a decrease of said measured values is preceded at an increase in a rate of said heartbeats.

2. A detection device as claimed in claim 1 wherein said blood flow velocity data includes data identifying a peak flow velocity of said at least one blood flow velocity wave, and wherein said control means comprises means for generating said signal indicating detection of venous pooling if a decrease of successive peak flow velocities is preceded by an increase in a rate of said heartbeats.

3. A detection device as claimed in claim 1 wherein said control means includes means for calculating a first derivative of each of said measured values, and wherein said control means comprises means for generating said signal indicating detection of venous pooling if a decrease of the respective first derivatives of successive measured values is preceded by an increase in a rate of said heartbeats.

4. A detection device as claimed in claim 1 wherein said control means comprises means for calculating an integral value of each of said successive occurrences of said at least one blood flow velocity wave, and for generating a signal indicating detection of venous pooling if a decrease of the respective integral values of successive blood flow velocity waves is preceded by an increase in a rate of said heartbeats.

5. A detection device as claimed in claim 1 wherein said control means comprises means for initiating a period, within which said sensor means is enabled for obtaining said blood flow velocity data, synchronized with said heartbeats.

6. A detection device as claimed in claim 1 wherein said means for obtaining heartbeat data comprises a cardiac lead having at least one electrode for sensing an intracardiac electrogram, and wherein said control means comprises means for enabling said sensor means for obtaining said blood flow velocity data at a time dependent on an occurrence of a predetermined event in said intracardiac electrogram.

7. A detection device for detecting venous pooling in a human body, comprising:
    a lead adapted for implantation in a subject and carrying sensor means for obtaining blood pressure data, said blood pressure data including data identifying at least one blood pressure wave produced after each heartbeat;
    means for obtaining heartbeat data identifying successive heartbeats of said subject; and
    control means, supplied with said blood pressure data and said heartbeat data, for identifying respective measured values of successive occurrences of said at least one blood pressure wave and for generating a signal indicating detection of venous pooling if a decrease of said measured values is preceded at an increase in a rate of said heartbeats.

8. A detection device as claimed in claim 7 wherein said blood pressure data includes data identifying a peak pressure of said at least one blood pressure wave, and wherein said control means comprises means for generating said signal indicating detection of venous pooling if a decrease of successive peak flow velocities is preceded by an increase in a rate of said heartbeats.

9. A detection device as claimed in claim 7 wherein said control means includes means for calculating a first derivative of each of said measured values, and wherein said control means comprises means for generating said signal indicating detection of venous pooling if a decrease of the respective first derivatives of successive measured values is preceded by an increase in a rate of said heartbeats.

10. A detection device as claimed in claim 7 wherein said control means comprises means for calculating an integral value of each of said successive occurrences of said at least one blood pressure wave, and for generating a signal indicating detection of venous pooling if a decrease of the respective integral values of successive blood pressure waves is preceded by an increase in a rate of said heartbeats.

11. A detection device as claimed in claim 7 wherein said control means comprises means for initiating a period, within which said sensor means is enabled for obtaining said blood pressure data, synchronized with said heartbeats.

12. A detection device as claimed in claim 7 wherein said means for obtaining heartbeat data comprises a cardiac lead having at least one electrode for sensing an intracardiac electrogram, and wherein said control means comprises means for enabling said sensor means for obtaining said blood pressure data at a time dependent on an occurrence of a predetermined event in said intracardiac electrogram.

13. A therapy device for preventing vasovagal syncope comprising:

a first cardiac lead carrying a first electrode, and adapted for implantation in a right atrium of a heart of a subject;

a second cardiac lead carrying a second electrode, and adapted for implantation in a right ventricle of a heart of a subject;

at least one of said first and second leads carrying sensor means for obtaining blood flow velocity data, said blood flow velocity data including data identifying at least one blood flow velocity wave produced after a heartbeat;

at least one of said first and second leads comprising means for obtaining heartbeat data identifying successive heartbeats of said subject;

control means, supplied with said blood flow velocity data and said heartbeat data, for identifying respective measured values of successive occurrences of said at least one blood flow velocity wave and for generating a signal indicating detection of venous pooling if a decrease of said measured values is preceded by an increase in a rate of said heartbeats; and pulse generator means, controlled by said control means, for emitting cardiac pacing pulses via at least one of said first and second leads, in response to said signal indicating detection of venous pooling.

14. A therapy device as claimed in claim 13 further comprising means for administering a controlled quantity of a drug to said heart in response to said signal indicating detection of venous pooling.

15. A therapy device as claimed in claim 14 wherein said means for administering a controlled quantity of a drug comprises said first cardiac lead, said first cardiac lead comprising a hollow channel therein terminating in an opening at a distal end of said first cardiac lead, and drug reservoir and administration means, in communication with said hollow channel, operated by said control means for releasing said controlled quantity of said drug into said hollow channel upon generation of said signal indicating detection of venous pooling.

16. A therapy device as claimed in claim 13 wherein said means for obtaining heartbeat data comprises means for sensing an intracardiac electrogram.

17. A therapy device as claimed in claim 13 wherein said blood flow velocity data include data respectively identifying an early diastolic filling wave and a late diastolic filling wave and wherein said control means comprises means for discriminating in said data between said early diastolic filling wave and said late diastolic filling wave, means for measuring a peak velocity of said early diastolic filling wave and a peak velocity of said late diastolic filling wave and means for calculating an acceleration and a deceleration of the respective peak velocities of said early diastolic filling wave and said late diastolic filling wave for use as said measured values.

18. A therapy device as claimed in claim 13 wherein said blood flow velocity data include data identifying a reversal flow wave caused by atrial contraction, a systolic wave caused by ventricular contraction, and a diastolic wave caused by ventricular relaxation, and wherein said control means comprises means for discriminating among the data respectively identifying said reversal flow wave, said systolic wave and said diastolic wave, means for measuring a peak velocity of said reversal flow wave, a peak velocity of said systolic wave and a peak velocity of said diastolic wave, and means for calculating an acceleration and a deceleration of each of said peak velocities of the respective reversal flow wave, systolic wave and diastolic wave as said measured values.

19. A therapy device as claimed in claim 13 wherein said control means comprises means for identifying a rapid increase of said heartbeat rate associated with an increase in said measured values.

20. A therapy device for preventing vasovagal syncope comprising:

a first cardiac lead carrying a first electrode, and adapted for implantation in a right atrium of a heart of a subject;

a second cardiac lead carrying a second electrode, and adapted for implantation in a right ventricle of a heart of a subject;

at least one of said first and second leads carrying sensor means for obtaining blood pressure data, said blood pressure data including data identifying at least one blood pressure wave produced after a heartbeat;

at least one of said first and second leads comprising means for obtaining heartbeat data identifying successive heartbeats of said subject;

control means, supplied with said blood pressure data and said heartbeat data, for identifying respective measured values of successive occurrences of said at least one blood pressure wave and for generating a signal indicating detection of venous pooling if a decrease of said measured values is preceded by an increase in a rate of said heartbeats; and pulse generator means, controlled by said control means, for emitting cardiac pacing pulses via at least one of said first and second leads, in response to said signal indicating detection of venous pooling.

21. A therapy device as claimed in claim 20 further comprising means for administering a controlled quantity of a drug to said heart in response to said signal indicating detection of venous pooling.

22. A therapy device as claimed in claim 21 wherein said means for administering a controlled quantity of a drug comprises said first cardiac lead, said first cardiac lead comprising a hollow channel therein terminating in an opening at a distal end of said first cardiac lead, and drug reservoir and administration means, in communication with said hollow channel, operated by said control means for releasing said controlled quantity of said drug into said hollow channel upon generation of said signal indicating detection of venous pooling.

23. A therapy device as claimed in claim 20 wherein said means for obtaining heartbeat data comprises means for sensing an intracardiac electrogram.

24. A therapy device as claimed in claim 20 wherein said blood pressure data include data respectively identifying an early diastolic filling wave and a late diastolic filling wave and wherein said control means comprises means for discriminating in said data between said early diastolic filling wave and said late diastolic filling wave, means for measuring a peak velocity of said early diastolic filling wave and a peak velocity of said late diastolic filling wave and means for calculating an acceleration and a deceleration of the respective peak velocities of said early diastolic filling wave and said late diastolic filling wave for use as said measured values.

25. A therapy device as claimed in claim 20 wherein said blood pressure data include data identifying a reversal flow wave caused by atrial contraction, a systolic wave caused by ventricular contraction, and a diastolic wave caused by ventricular relaxation, and wherein said control means comprises means for discriminating among the data respectively identifying said reversal flow wave, said systolic wave and said diastolic wave, means for measuring a peak velocity of said reversal flow wave, a peak velocity of said systolic wave and a peak velocity of said diastolic wave, and means for calculating an acceleration and a deceleration of each of said peak velocities of the respective reversal flow wave, systolic wave and diastolic wave as said measured values.

26. A therapy device as claimed in claim 20 wherein said control means comprises means for identifying a rapid increase of said heartbeat rate associated with an increase in said measured values.

* * * * *